(12) United States Patent
Schwab

(10) Patent No.: US 10,060,858 B2
(45) Date of Patent: Aug. 28, 2018

(54) DEVICE AND METHOD FOR MEASURING DISTORTION DEFECTS IN A MANUFACTURED FLOAT GLASS STRIP

(71) Applicant: GRENZEBACH MASCHINENBAU GMBH, Asbach-Baeumenheim (DE)

(72) Inventor: Leonhard Schwab, Butterblumenweg (DE)

(73) Assignee: GRENZEBACH MASCHINENBAU GMBH, Asbach-Baeumenheim (DE)

( * ) Notice: Subject to any disclaimer, the term of this patent is extended or adjusted under 35 U.S.C. 154(b) by 0 days.

(21) Appl. No.: 15/313,867

(22) PCT Filed: May 29, 2015

(86) PCT No.: PCT/DE2015/000269
§ 371 (c)(1),
(2) Date: Nov. 23, 2016

(87) PCT Pub. No.: WO2015/188802
PCT Pub. Date: Dec. 17, 2015

(65) Prior Publication Data
US 2017/0199133 A1    Jul. 13, 2017

(30) Foreign Application Priority Data
Jun. 10, 2014   (DE) .......... 10 2014 008 596

(51) Int. Cl.
*G01N 21/89*    (2006.01)
*G01N 21/896*   (2006.01)

(52) U.S. Cl.
CPC ....... *G01N 21/896* (2013.01); *G01N 21/8903* (2013.01); *G01N 2201/062* (2013.01)

(58) Field of Classification Search
CPC .................. G01N 21/896; G01N 2201/062
See application file for complete search history.

(56) References Cited

U.S. PATENT DOCUMENTS

| | | | | |
|---|---|---|---|---|
| 5,452,079 A | * | 9/1995 | Okugawa | G01N 21/896 250/559.42 |
| 2010/0213063 A1 | * | 8/2010 | Zenhausern | G01N 21/645 204/452 |

(Continued)

FOREIGN PATENT DOCUMENTS

| DE | 4139094 | 6/1993 |
|---|---|---|
| DE | 19813072 | 9/1999 |

(Continued)

OTHER PUBLICATIONS

English Machine Translation of Hatzenbuehler, DE102008019084 (A1)—Oct. 29, 2009.*

*Primary Examiner* — Dominic J Bologna
(74) *Attorney, Agent, or Firm* — Duane Morris LLP; J. Rodman Steele, Jr.; Gregory M. Lefkowitz

(57) ABSTRACT

The invention relates to a method and a device for the rapid and reliable measuring of distortion defects in a manufactured float glass strip, having the following features: a) a linear inset LED light source (5) sweeping the breadth of the glass strip (4) to be examined, said light source having LEDs that are tightly packed one next to the other below a glass strip (4) to be examined, b) a linear cylindrical lens 8) which is arranged in parallel to the entire length of the inset LED light source (5) and the distance of which to the inset LED light source (5) is continuously variable, c) a light source (2) arranged above the glass strip (4), d) an array of at least 4 CCD cameras arranged above the glass strip (4), and a two-stage parallel signal evaluation unit.

5 Claims, 6 Drawing Sheets

(56) References Cited

U.S. PATENT DOCUMENTS

Figure 1:
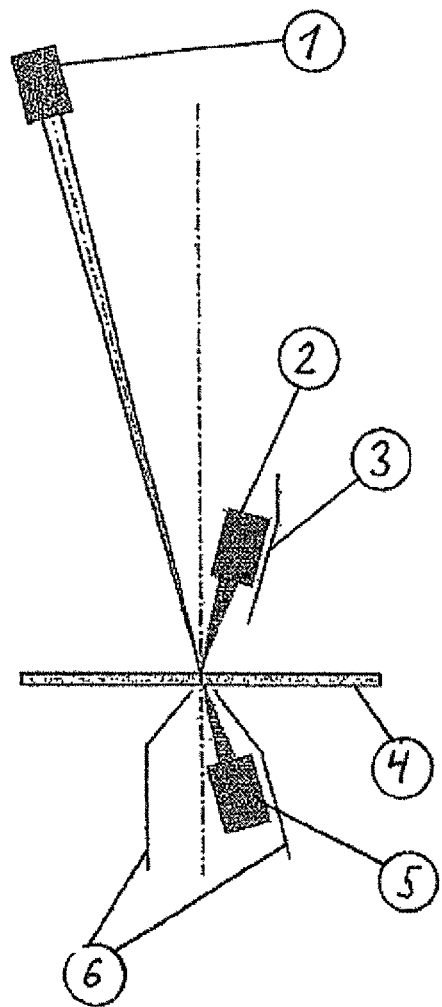

2011/0141270 A1* 6/2011 Miyake .............. G01N 21/896
   348/125
2014/0152808 A1* 6/2014 Ullrich .............. G01N 21/896
   348/131

FOREIGN PATENT DOCUMENTS

| DE | 102008019084 | 10/2009 |
|----|--------------|---------|
| DE | 102010046433 | 3/2012  |
| DE | 102011109793 | 2/2013  |
| EP | 0576011      | 6/1993  |
| EP | 0726457      | 8/1996  |
| EP | 1288651      | 3/2003  |
| EP | 2253948      | 11/2010 |
| FR | 2983583      | 7/2013  |
| WO | 2013020542   | 2/2013  |

* cited by examiner

Fig. 2
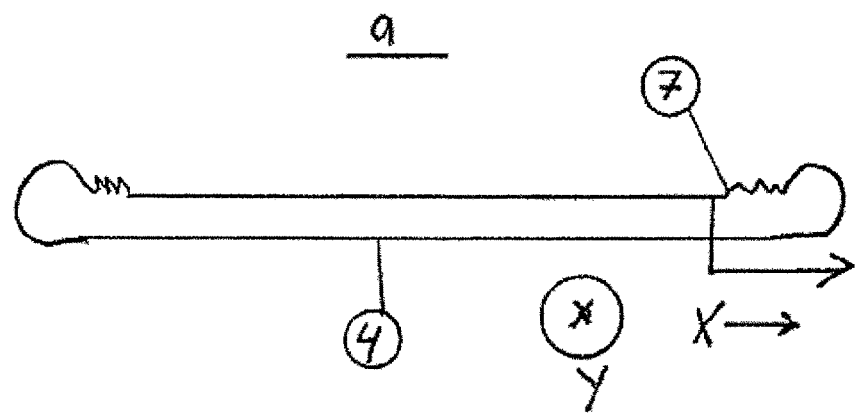
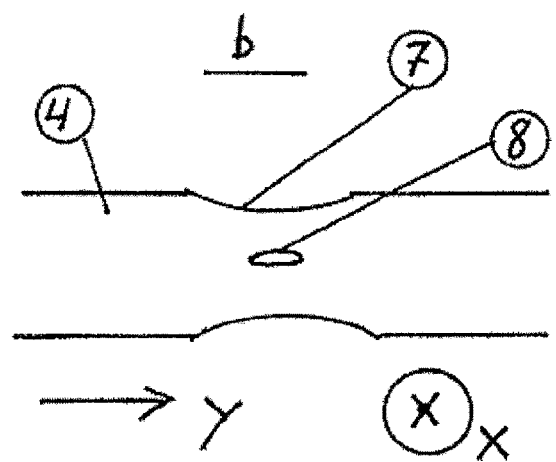

Fig. 4
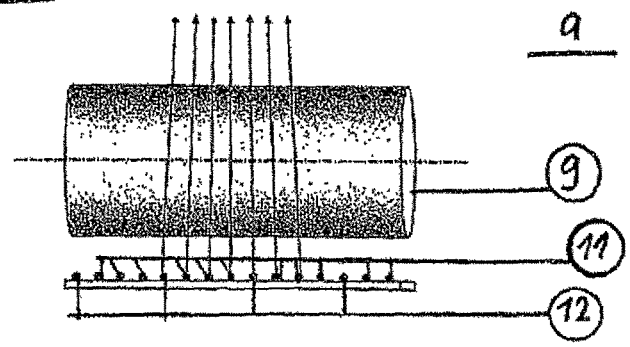
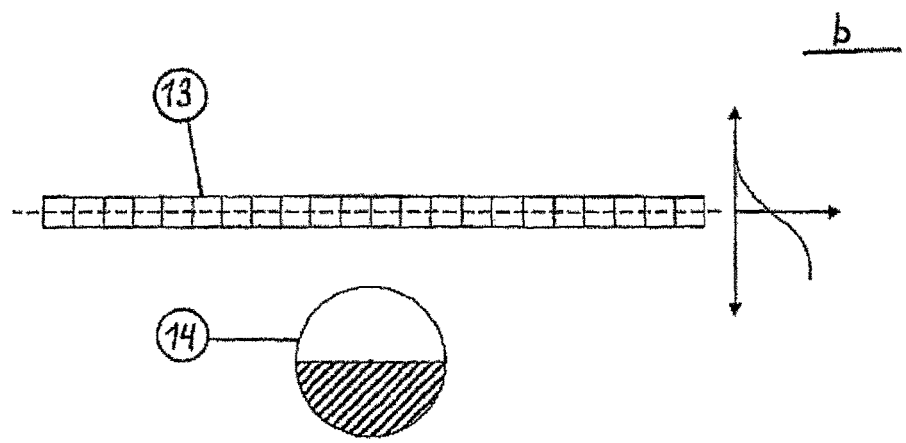
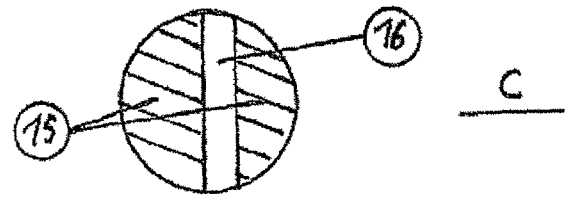

Fig. 5
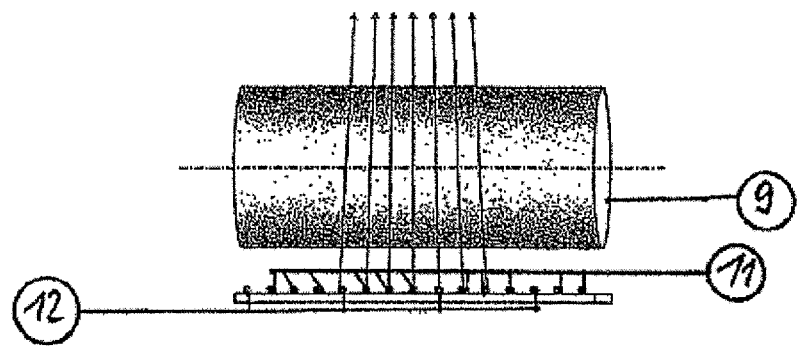
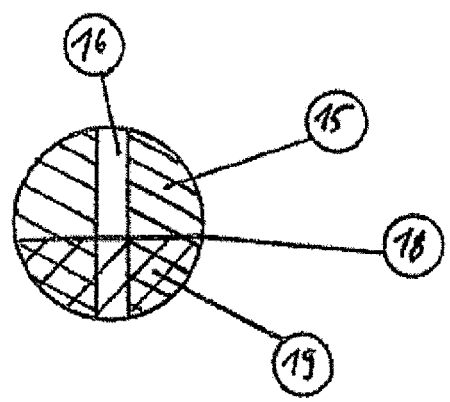

DEVICE AND METHOD FOR MEASURING DISTORTION DEFECTS IN A MANUFACTURED FLOAT GLASS STRIP

CROSS-REFERENCE TO RELATED APPLICATIONS

This application is a § 371 national stage entry of International Application No. PCT/DE2015/000269, filed May 29, 2015, which claims priority to German Patent Application No. 10 2014 008 596.1, filed Jun. 10, 2014, the entire contents of which are incorporated herein by reference.

The invention relates to a device and a method for rapidly and reliably measuring distortion defects in a manufactured float glass strip. A whole-area measurement of the thickness variation and of the refractive power variation is possible in this case.

With regard to the prior art, a method and a device for determining optical defects are known from the patent specification EP 1 288 651 B1.

In this case, the preamble of patent claim 1 proceeds from a device for determining optical defects, in particular in the refractive power, in large-area sheets of a transparent material such as glass by means of an evaluation of the observed image, comprising the following features:

A light source for projecting a defined pattern of regular sequences, wherein the sequences comprise at least two different light intensities; means for arranging the sheet in the beam path of the projection, and, as a further feature, a camera, wherein sequences of the pattern are directed onto pixels of the camera. Said patent specification is based on the objective, inter alia, of specifying a device according to the preamble of patent claim 1 which can be used to determine optical defects in at least one dimension of a sheet.

For this purpose, according to the indications in the characterizing part of patent claim 1, what was afforded protection was that the light source is a luminous wall embodied as a luminous matrix and comprising a multiplicity of LEDs which can be driven selectively, preferably in lines and/or columns.

With regard to the prior art, a device and a method for detecting defects in continuously produced float glass are furthermore known from DE 10 2010 046 433 B4, registered in the name of the applicant. This document is based on the objective of presenting a device and a method for continuously detecting and monitoring the formation of defects, for example in the form of inclusions, bubbles or similar undesired phenomena, during the ongoing process for producing a strip of liquid glass, so-called float glass.

In order to achieve said objective, according to the indications in patent claim 1 of said document, what was afforded protection was that a device for detecting defects in a continuously produced float glass strip by means of the testing of a glass ribbon that runs transversely with respect to the conveying direction and is observed in transmitted light is characterized in that it has the following features:

a) a modularly constructed securing bridge for scanning sensors which is designed in accordance with the width of the float glass strip to be tested, wherein the scanning sensors cover said width without gaps in respect of their acquisition region and the float glass strip is transilluminated without gaps by means of a linear illuminant with a constant luminous flux and an adjacent linear illuminant with an oscillating luminous flux, b) an adjusting unit assigned to each scanning sensor, said adjusting unit enabling a variation of the position of each scanning sensor along the three spatial coordinates in positive and negative directions, c) a target unit assigned to each scanning sensor, said target unit being introducible by pivoting and being in the form of an artificial measurement plane for accurately aligning a scanning sensor with the surface of the float glass strip, d) a cooling unit for cooling the illuminants.

Furthermore, the document WO 2013/020542 A1 is known from the prior art, said document likewise being attributed to the applicant and describing a method and a device for reliably detecting material defects in transparent material. Said document is based on the objective of presenting a device and a method with which all possible defects which can occur in transparent material, in particular glass, can be reliably detected and classified. In addition, the intention is to enable the user at any time to ascertain that the reliability of the operation of the device, or of the method, is ensured.

This objective is achieved in accordance with the indications in patent claim 1, with a device for reliably detecting material defects in a continuously produced strip of transparent material by means of the testing of a ribbon of a strip of said material that runs transversely with respect to the conveying direction and is observed in transmitted light and reflected light, which device is characterized by the following features:

a) a securing gantry with the width of the transparent material to be tested serves as a carrier of linear cameras, wherein the linear cameras cover said width without gaps in respect of their acquisition region and the material strip is transilluminated without gaps by means of a linear illuminant with a constant luminous flux and an adjacent linear illuminant with an oscillating luminous flux, and wherein an additional brightfield illumination illuminates the inspected ribbon in reflected light, b) the securing gantry additionally serves as a carrier of further linear cameras, the optical axes of which are slightly inclined with respect to that of the linear cameras, wherein the linear cameras also cover said width without gaps in respect of their acquisition region, wherein the linear cameras observe a line grating situated on the surface of the illuminant, and wherein the examined ribbon is illuminated in reflected light by means of a dark-field illumination, c) a device for monitoring the function of the illuminants and the cameras.

The present invention and the associated method are based on the object of presenting a device and a method for the improved detection and classification of material defects in a moving transparent medium.

This object is achieved by means of a device as claimed in patent claim 1

A device for rapidly and reliably measuring distortion defects in a manufactured float glass strip, comprising the following features:

a) a linear inset LED light source (5) transilluminating from below the width of the glass strip (4) to be examined, said light source having LEDs arranged closely alongside one another, wherein at least two types of LEDs having different wavelengths in an arbitrary sequence are used, and the inset LED light source (5) is inclined at an acute angle with respect to the examination plane, b) a cylindrical lens element (8) arranged linearly and parallel to the entire length of the inset LED light source (5), the distance between said cylindrical lens element and the inset LED light source (5) being adjustable in a continuously variable manner, wherein said cylindrical lens element is arranged below the glass strip (4) in the plane of the beam path between the inset LED light source (5) and an arrangement of four CCD cameras (1) arranged in a series, c) a light source (2) arranged above the glass strip (4), wherein said light source is inclined at an acute angle, measured from the vertical in the examination plane, with respect to the same side as the inset LED light source (5), d) an arrangement of at least four CCD cameras arranged above the glass strip (4), wherein the lenses of said cameras can optionally be equipped with a slit diaphragm (16), a blade diaphragm (18) and/or a dichroic and/or a trichroic filter, e) a two-stage parallel signal evaluation, wherein bitmaps from all channels are processed in parallel and further data from the production line are concomitantly included.

What is furthermore claimed is
that LEDs having a wavelength corresponding to the color green and LEDs having a wavelength corresponding to the color blue are used.

What is likewise claimed is that the inset LED light source (5) and the CCD cameras (1) lie opposite one another relative to the glass strip (4) to be examined and are inclined with respect to one another in their optical connecting axis such that they are reliably protected against damage by means of a lower light source protection (6) mounted areally in front and by means of an upper light source protection (3) mounted areally in front.

and a method as claimed in patent claim 4

A method for rapidly and reliably measuring distortion defects in a manufactured float glass strip, comprising the following features:

a) the glass strip (4) to be examined is irradiated by means of a linear inset LED light source (5) transilluminating from below the width of the glass strip (4) to be examined, said light source having LEDs arranged closely alongside one another, wherein at least two types of LEDs having different wavelengths in an arbitrary sequence are used, and the inset LED light source (5) is inclined at an acute angle with respect to the examination plane, b) by means of the set-up of a cylindrical lens element (8) arranged linearly and parallel to the entire length of the inset LED light source (5), the distance between said cylindrical lens element and the inset LED light source (5) being adjustable in a continuously variable manner, wherein said cylindrical lens element is arranged below the glass strip (4) in the plane of the beam path between the inset LED light source (5) and an arrangement of at least four CCD cameras (1) above the glass strip (4), the beam path is focused such that a point imaging of an LED in the measurement plane of a CCD camera (1) arranged above the glass strip (4) is carried out, c) a two-stage parallel signal evaluation is carried out during the progression past the glass strip (4), wherein bitmaps from all channels are processed in parallel and further data from the production line are concomitantly included and a particular accuracy of the determination of defects is achieved by means of a particular mathematical algorithm.

What is additionally claimed is that LEDs having a wavelength corresponding to the color green and LEDs having a wavelength corresponding to the color blue are used.

We furthermore claim that the inset LED light source (5) and the CCD cameras (1) lie opposite one another relative to the glass strip (4) to be examined and are inclined with respect to one another in their optical connecting axis such that they are reliably protected against damage by means of a lower light source protection (6) mounted areally in front and by means of an upper light source protection (3) mounted areally in front. Likewise a computer program comprising a program code for performing the method steps when the program is executed in a computer. What is furthermore claimed is a machine-readable carrier comprising the program code of a computer program for performing the method when the program is executed in a computer.

The invention is described in greater detail below.

Specifically in the figures here:

FIG. 1: shows an illustration of the device according to the invention

FIG. 2: shows an overview of relevant glass defects

Figure 3:
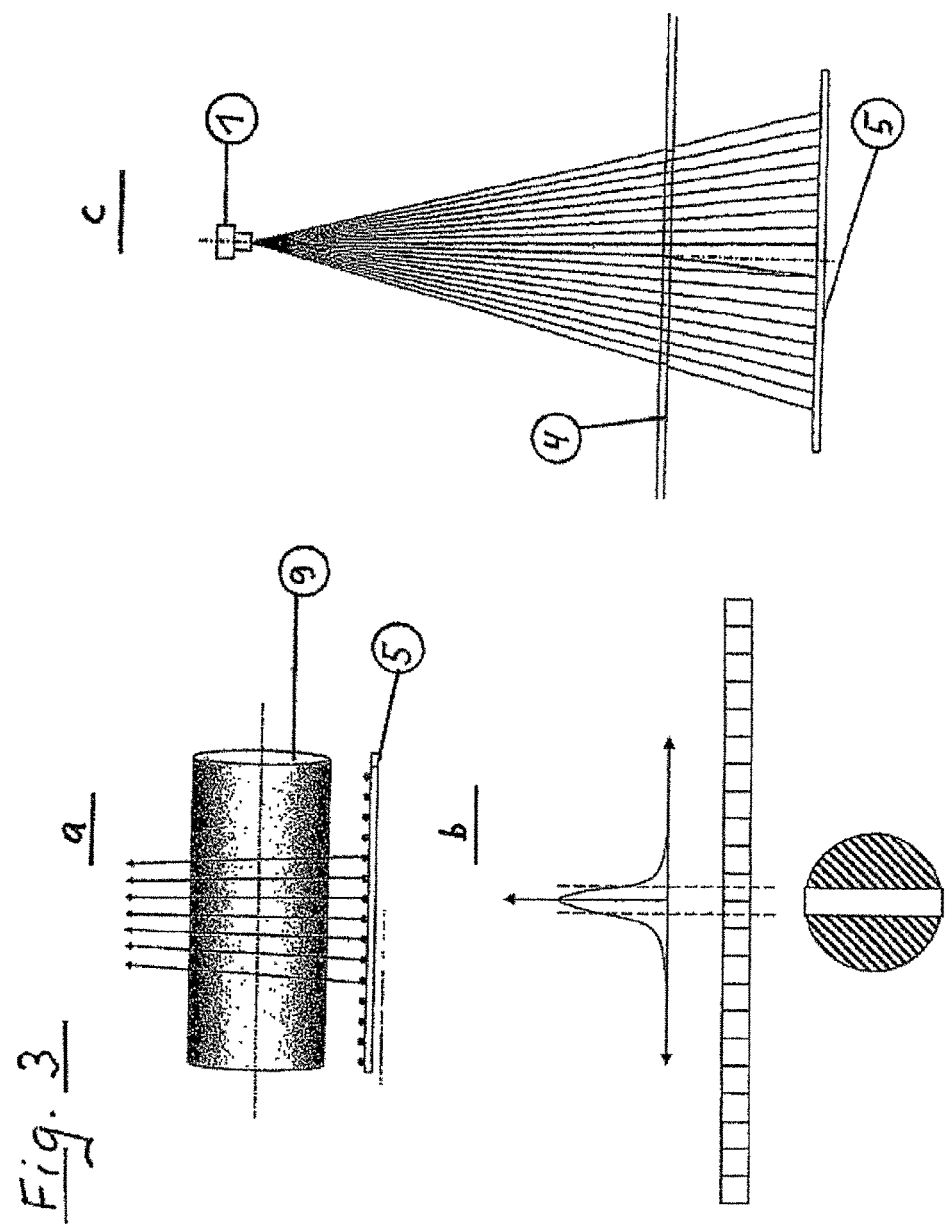

FIG. 3: shows the principle of light mixing and focusing

FIG. 4: shows the use of different wavelengths as a measurement principle

FIG. 5: shows the use of a trichroic diaphragm

Figure 6:
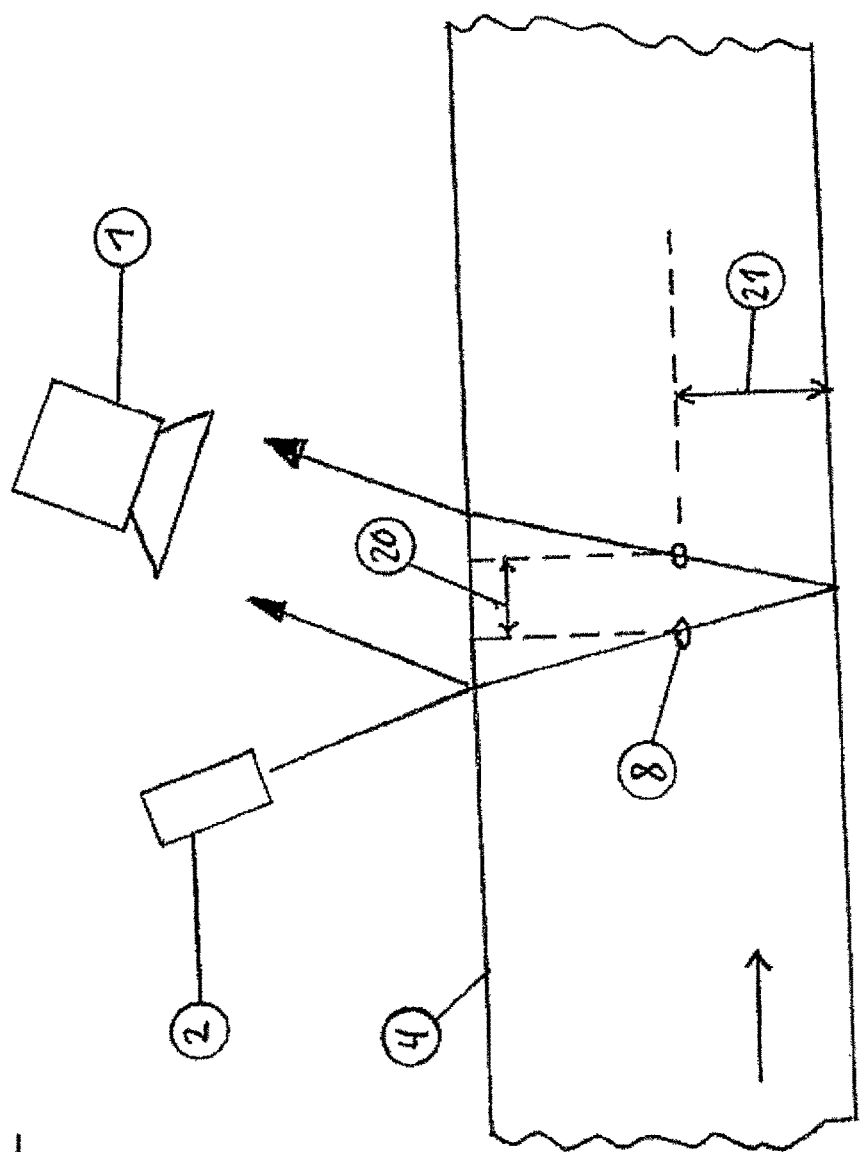

FIG. 6: shows a signal evaluation with regard to the position of bubbles in the glass strip.

FIG. 1 shows an illustration of the device according to the invention.

4 here denotes the glass strip to be examined or the respective glass sheet. In this illustration, the CCD camera 1 represents one of four or more CCD cameras which are arranged alongside one another and which jointly, when arranged at a specific height above the glass strip, optically acquire the entire width of the glass strip to be examined. A light source 2 illuminates the glass strip from above in an examination plane, illustrated in a dashed manner. 5 identifies a linear inset LED light source, consisting of a multiplicity of LEDs arranged alongside one another. An upper light source protection 3 and a bipartite lower light source protection 6 provide for the protection of the fail-safe LEDs. The installation shown is also thus very immune to interference and long-lived.

FIG. 2 shows an overview of relevant glass defects. FIG. 2a) shows in sectional view a glass strip freshly emerging from the melt of the kiln, after the cooling zone. In this case, in the center the usable region of the glass strip is represented by 4, while on the left and right the two edge regions, in a manner caused by the manufacturing process, have bulges and build-ups which represent distorted regions 7, are therefore economically unusable and are separated off later. The running direction of the glass strip is designated here by Y, and the direction running at a right angle transversely with respect to the running direction is designated by X.

FIG. 2b) shows an inclusion 8 detected in the usable region of the glass strip 4, said inclusion representing, at the surface of the glass strip 4 on one or both sides, an—exaggerated in the illustration—distorted region 7 (flattened portion or thickening) of the glass strip 4. The running direction Y of the glass strip is assumed here to be in the transverse direction with respect to the plane of the drawing.

FIG. 3 shows the principle of light mixing and focusing.

FIG. 3a) shows an excerpt from a linear inset LED light source 5, in the case of which light beams emerging from some LEDs can be seen, which light beams pass through a cylindrical lens element 9, then pass through the glass strip to be examined and are finally registered in a CCD camera 1. The illustration of the cylindrical lens element 9 here likewise shows an excerpt therefrom. In this case, the LED light source 5 and the structure of the cylindrical lens element 9 shown extend over the entire width of the glass strip 4 to be examined.

FIG. 3*c*) illustrates this substantive matter in principle without the beam path through the cylindrical lens element 9.

The principle shown of LED collimation by means of the cylindrical lens element 9 enables large distances of the LED illumination without significant losses of intensity and a high sensitivity with regard to distortion defects to be detected. In this case, the beam path between the, substantially point, light source as represented by an LED and the capture plane of a CCD camera 1 can be adapted in almost any desired fashion by means of a variation of the distance between the LED light source 5 and the cylindrical lens element 9.

FIG. 3*b*) illustrates the distribution of the beam intensity of an LED that is registered in a CCD camera. The position of the peak on the CCD linear array is dependent on the glass thickness or on the thickness gradient or refractive power gradient in the X-direction of the glass. Accurate measurement of the position shift in comparison with defect-free glass yields the local distortion of the glass in the X-direction.

A CCD camera 1 has available the width of a pixel as smallest resolution the possibility for registering defects to be detected in the glass strip. The width of a pixel is approximately 10 µm. Since the area of the distribution curve illustrated in FIG. 3*b*, which corresponds approximately to a so-called Gaussian distribution, is greater than a pixel, in order to achieve a high sensitivity of the measuring system according to the invention it is necessary to determine the position of the so-called centroid of this distribution. This is achieved by means of a specific mathematical algorithm. It is thus possible to determine the position of the centroid on the CCD linear array with a sub-pixel accuracy, for example of 0.1 pixel (1 µm).

The local distortion can be measured with the arrangement at many points for example with the distance of delta −x. All local distortions taken together yield a complete transverse profile of the variation in the X-direction. On account of the whole-area measurement by means of successive transverse profiles and the continuity of the glass surface, the variation in the Y-direction can also be calculated from the variation in the X-direction.

FIG. 4 shows the use of different wavelengths as a measurement principle.

FIG. 4*a*) reveals an image comparable to that in FIG. 3*a*), but with the difference that instead of a linear juxtaposition of one specific type of LEDs, two thereof which are different with regard to the emitted wavelength are shown as LED light source 5. In this case, green LEDs are identified by the reference sign 11, while blue LEDs are designated by 12. The fact that LEDs having different wavelengths are used is essential here. LEDs having green coloration and LEDs having blue coloration were used here merely by way of example.

This enables the set-up of two or more measurement channels to be operated simultaneously, but differently and separately.

FIG. 4*b*) illustrates the intensity distribution transversely with respect to the CCD linear array, such as results from the use of a suitable blade diaphragm. With this combination of a plurality of different LEDs in an illumination, blue and green, for example, are registered independently of different linear arrays with in each case adapted aperture and gain.

FIG. 5 shows the use of a trichroic diaphragm. The illustration of the relationships in FIG. 5 corresponds largely to the illustration in FIG. 4. FIG. 5 again shows an illumination of the glass strip to be examined by means of LEDs of different wavelengths.

In the case of the trichroic diaphragm in FIG. 5, what is of importance is supervising the image field and the intensity for the different wavelengths:

For the color red in reflection, the intensity is the lowest (glass has only 4% reflectance per surface, i.e. only 8% in total). Therefore, the entire diaphragm opening is required for the color red.

In the transmittance of glass this means: 100%−8%=92%. Therefore, it is possible to reduce the luminous flux with a smaller diaphragm opening (diaphragm area).

A very small opening suffices for measuring the distortion with the blue LEDs, since all that is of importance is seeing the light spots of the LEDs on the CCD linear array. This is realized by means of the slit diaphragm. The shaping as a slit has the advantage that the beam deflection in the Y-direction has no influence. The slit does not serve for narrowing the field of view.

For the green wavelength, besides the luminous flux the field of view is also intended to be restricted, such that a beam deflection in the Y-direction additionally affects the intensity.

In the present example, the green LEDs preferably serve for measuring the beam deflection in the direction of the running glass strip (Y-direction). On account of the whole-area measurement and the continuity of the glass surface, the variation in the X-direction can also be calculated from the detection of the variation in the Y-direction.

The combination of the demonstrated LED illumination with a trichroic diaphragm enables a whole-area measurement of the thickness and also thickness variation and refractive power variation.

FIG. 6 shows a signal evaluation with regard to the position of bubbles in the glass strip.

FIG. 6 shows a glass strip 4 having an inclusion (for example an air bubble) 8 that moves progressively in the course of the manufacturing process, this movement being tracked by means of a CCD camera 1.

Alongside distortions, inclusions are among the most important types of defect which must be classified in the manufacture of glass. Many inclusions cause distortions and can thereby be characterized as relevant defects. Small inclusions in thick glasses, in particular, do not cause any distortion, however. Therefore, it is necessary to employ other methods for classifying them.

For detection purposes, in this case the glass strip 4 is illuminated by a light source 2 with red light emission at an angle of approximately 15 degrees with respect to the perpendicular. In this case, the light beam emitted by the light source 2 is reflected and refracted once at the surface of the glass strip 4, passed on through the glass strip, reflected at the lower surface of the glass strip 4 and then refracted again before emerging from the glass strip 4 and can then be measured. An inclusion (e.g. air bubble) interrupts the light beam on the outgoing path and on the return path after reflection. In the CCD linear array, the inclusion thus appears doubled with a shadow or echo while the glass strip continues to move. From the measurement of the temporal spacing of the defect image and the echo thereof, together with the strip speed it is then possible to calculate the so-called echo distance and the respective height position of this inclusion (air bubble) 8.

A two-stage parallel signal evaluation is carried out during the progression past the glass strip (4), wherein bitmaps from all channels are processed in parallel and further data from the production line are concomitantly included and a particular accuracy of the determination of defects is achieved by means of a particular mathematical algorithm.

LIST OF REFERENCE SIGNS

1 CCD camera
2 Light source (red)
3 Upper light source protection
4 Glass strip or glass sheet
5 Inset LED light source
6 Lower light source protection
7 Distorted region
8 Inclusion or air bubble
9 Cylindrical lens element
10 Peak
11 Green LEDs
12 Blue LEDs
13 CCD camera linear array
14 Imaging of the cylindrical lens element
15 Dichroic filter (stops blue)
16 Slit diaphragm
17 Video signal green (uniform intensity)
18 Blade diaphragm
19 Trichroic filter
20 Echo distance
21 Height position of an inclusion in the glass strip

The invention claimed is:

1. A device for rapidly and reliably measuring distortion defects in a manufactured float glass strip, comprising:
 a linear inset LED light source (5) positioned below the manufactured float glass strip (4) to be examined,
  said linear inset LED light source having LEDs arranged alongside one another,
  wherein the linear inset LED light source comprises at least two types of LEDs having different wavelengths in an arbitrary sequence, and
  the linear inset LED light source (5) is inclined at an acute angle, measured from a perpendicular plane with respect to the manufactured float glass strip,
 a cylindrical lens element (9) arranged linearly and parallel to the entire length of the linear inset LED light source (5), the distance between said cylindrical lens element and the linear inset LED light source (5) being adjustable in a continuously variable manner,
  wherein said cylindrical lens element is arranged below the manufactured float glass strip (4) in the plane of a beam path between the linear inset LED luminaire (5) and an arrangement of at least four CCD cameras (1) arranged in a series above the manufactured float glass strip (4),
 a light source (2) arranged above the manufactured float glass strip (4),
  wherein said light source (2) is inclined at an acute angle, measured from a perpendicular plane with respect to the manufactured float glass strip, and positioned on the same side of the perpendicular plane as the linear inset LED light source (5),
 wherein lenses of said at least four CCD cameras are optionally equipped with a slit diaphragm (16), a blade diaphragm (18) and/or a dichroic and/or a trichroic filter,
 a controller adapted to carry out a two-stage parallel signal evaluation, wherein bitmaps from all channels are processed in parallel and further data are concomitantly included,
 wherein the linear inset LED light source (5) and the CCD cameras (1) lie opposite one another relative to the glass strip (4) to be examined,
 wherein the linear inset LED light source (5) and the CCD cameras (1) are inclined with respect to one another in their optical connecting axis, and
 wherein a lower light source protection element (6) is mounted areally in front of the linear inset LED light source (5), and an upper light source protection element (3) is mounted areally in front the CCD cameras (1).

2. The device as claimed in claim 1, wherein the LEDs have a wavelength corresponding to the color green, blue, or both.

3. A method for measuring distortion defects in a manufactured float glass strip, comprising:
 irradiating the manufactured float glass strip (4) to be examined with a linear inset LED light source (5) arranged below the manufactured float glass strip (4) to be examined,
  said linear inset LED light source having LEDs arranged alongside one another,
  wherein the linear inset LED light source comprises at least two types of LEDs having different wavelengths in an arbitrary sequence, and
  the linear inset LED light source (5) is inclined at an acute angle, measured from a perpendicular plane with respect to the manufactured float glass strip to be examined,
 adjusting in a continuously variable manner a distance between the linear inset LED light source (5) and a cylindrical lens element (8) arranged linearly and parallel to the entire length of the linear inset LED light source (5),
  wherein said cylindrical lens element is arranged below the manufactured float glass strip (4) in the plane of a beam path between the linear inset LED light source (5) and an arrangement of at least four CCD cameras (1) arranged in a series above the manufactured float glass strip (4),
 focusing the beam path to carry out a point imaging of an LED in a measurement plane of a CCD camera (1) arranged above the manufactured float glass strip (4),
 progressing the manufactured float glass strip (4) in a production line, and
 conducting a two-stage parallel signal evaluation of the manufactured float glass strip (4), wherein bitmaps from all channels are processed in parallel and further data from the production line are concomitantly included,
 wherein the linear inset LED light source (5) and the CCD cameras (1) lie opposite one another relative to the glass strip (4) to be examined,
 wherein the linear inset LED light source (5) and the CCD cameras (1) are inclined with respect to one another in their optical connecting axis, and
 wherein a lower light source protection element (6) is mounted areally in front of the linear inset LED light source (5), and an upper light source protection element (3) is mounted areally in front the CCD cameras (1).

4. The method as claimed in claim 3, wherein LEDs having a wavelength corresponding to the color green and LEDs having a wavelength corresponding to the color blue are used.

5. A machine-readable carrier comprising a non-transitory program code of a computer program for performing the method as claimed in claim 3 when the program is executed in a computer.

* * * * *

UNITED STATES PATENT AND TRADEMARK OFFICE
CERTIFICATE OF CORRECTION

PATENT NO. : 10,060,858 B2
APPLICATION NO. : 15/313867
DATED : August 28, 2018
INVENTOR(S) : Leonhard Schwab Page 1 of 1

It is certified that error appears in the above-identified patent and that said Letters Patent is hereby corrected as shown below:

On the Title Page

Column 1, Line 8, please replace Inventor:
"Leonhard SCHWAB, Butterblumenweg (DE)"
With:
"Leonhard SCHWAB, München (DE)"

Signed and Sealed this
Eleventh Day of December, 2018

Andrei Iancu
*Director of the United States Patent and Trademark Office*